(12) United States Patent
Jarvis et al.

(10) Patent No.: US 8,025,909 B2
(45) Date of Patent: Sep. 27, 2011

(54) USE OF HERBS IN HAIR RELAXATION

(75) Inventors: David Jarvis, Jacksonville, FL (US); Lauren Kelly, Jacksonville, FL (US)

(73) Assignee: Roux Laboratories Inc.

( * ) Notice: Subject to any disclaimer, the term of this patent is extended or adjusted under 35 U.S.C. 154(b) by 0 days.

(21) Appl. No.: 12/176,285

(22) Filed: Jul. 18, 2008

(65) Prior Publication Data

US 2010/0015075 A1   Jan. 21, 2010

(51) Int. Cl.
*A61K 36/00* (2006.01)
*A61K 36/10* (2006.01)
*A61K 36/13* (2006.01)
*A61K 36/28* (2006.01)
*A61K 38/45* (2006.01)

(52) U.S. Cl. ........ 424/737; 424/725; 424/774; 424/778; 424/770; 424/762; 424/732

(58) Field of Classification Search .......... None
See application file for complete search history.

(56) References Cited

U.S. PATENT DOCUMENTS

| | | | | |
|---|---|---|---|---|
| 5,077,042 A | * | 12/1991 | Darkwa et al. | 424/70.2 |
| 5,639,449 A | * | 6/1997 | Syed et al. | 424/70.17 |
| 7,205,009 B2 | * | 4/2007 | Stass | 424/730 |
| 2003/0115686 A1 | * | 6/2003 | Grey | 8/405 |
| 2007/0041921 A1 | | 2/2007 | Neill | |
| 2008/0057015 A1 | * | 3/2008 | Oblong et al. | 424/70.2 |

OTHER PUBLICATIONS

Hansen, Inge "African Pride: Colomer USA seeks to create new excitement in the relaxer category with the relaunch of its African Pride No-Lye Relaxers." Beauty Store Business, Oct. 2007, p. 80-82.
International Search Report and Written Opinion from International Application No. PCT/US09/51144 dated Sep. 10, 2009.

* cited by examiner

*Primary Examiner* — Christopher R Tate
*Assistant Examiner* — Deborah A. Davis
(74) *Attorney, Agent, or Firm* — Pillsbury Winthrop Shaw Pittman LLP (57) ABSTRACT

Compositions and methods for relaxing human hair with minimal damage to the hair comprising the steps of (a) preparing an aqueous mixture having a pH of at least 11 comprising (i) at least one base; and (ii) a pre-selected blend of dehydrated herbs; (b) applying the mixture to human hair for a period of time sufficient to effect a desired amount of relaxation; and (c) removing the mixture from the hair with a rinsing liquid.

15 Claims, 4 Drawing Sheets

| NO RELAXATION ONLY 2 SHAMPOOS |||
| --- | --- | --- |
| STRAND | GROUP # | BREAK LOAD (GMF) |
| 26A | 6 | 74.3 |
| 26B | 6 | 65.1 |
| 27A | 6 | 64.5 |
| 27B | 6 | 78.7 |
| 28A | 6 | 61.9 |
| 28B | 6 | 53.4 |
| 29A | 6 | 56.0 |
| 29B | 6 | 77.5 |
| 30A | 6 | 40.3 |
| 30B | 6 | 32.0 |
| | AVERAGE | 60.4 |
| | MIN | 32.0 |
| | MAX | 78.7 |

FIGURE 1

| RELAXED WITH NO HERBS |||
| --- | --- | --- |
| STRAND | GROUP # | BREAK LOAD (GMF) |
| 6A | 2 | 29.8 |
| 6B | 2 | 28.9 |
| 7A | 2 | 44.9 |
| 7B | 2 | 23.9 |
| 8A | 2 | 30.2 |
| 8B | 2 | 11.1 |
| 9A | 2 | --- |
| 9B | 2 | 40.8 |
| 10A | 2 | 65.4 |
| 10B | 2 | 43.8 |
| | AVERAGE | 32.1 |
| | MIN | 11.1 |
| | MAX | 65.4 |

FIGURE 2

| CONTROL –RELAXED WITH HERBS | | |
|---|---|---|
| STRAND | GROUP # | BREAK LOAD (GMF) |
| 1A | 1 | 36.7 |
| 1B1 | 1 | 38.4 |
| 1B2 | 1 | 64.4 |
| 2A | 1 | 71.5 |
| 2B | 1 | 62.0 |
| 3A | 1 | 56.1 |
| 3B | 1 | 31.9 |
| 4A | 1 | --- |
| 4B | 1 | 67.2 |
| 5A | 1 | 56.8 |
| 5B | 1 | 49.4 |
| | AVERAGE | 49.0 |
| | MIN | 31.9 |
| | MAX | 71.5 |

FIGURE 3

| RELAXED WITH 2X HERBS | | |
|---|---|---|
| STRAND | GROUP # | BREAK LOAD (GMF) |
| 11A | 3 | 55.1 |
| 11B | 3 | 59.3 |
| 12A | 3 | 86.0 |
| 12B | 3 | 32.6 |
| 13A | 3 | 68.8 |
| 13B | 3 | 62.3 |
| 14A | 3 | 66.4 |
| 14B | 3 | 50.4 |
| 15A | 3 | 48.4 |
| 15B | 3 | 68.0 |
| | AVERAGE | 59.7 |
| | MIN | 32.6 |
| | MAX | 86.0 |

FIGURE 4

| RELAXED WITH 4X HERBS |||
|---|---|---|
| STRAND | GROUP # | BREAK LOAD (GMF) |
| 16A | 4 | 47.3 |
| 16B | 4 | --- |
| 17A | 4 | 52.3 |
| 17B | 4 | 50.1 |
| 18A | 4 | 28.8 |
| 18B | 4 | 34.4 |
| 19A | 4 | 49.1 |
| 19B | 4 | 18.4 |
| 20A | 4 | 69.8 |
| 20B | 4 | 30.6 |
| | AVERAGE | 42.3 |
| | MIN | 18.4 |
| | MAX | 69.8 |

FIGURE 5

| RELAXED WITH 10X HERBS |||
|---|---|---|
| STRAND | GROUP # | BREAK LOAD (GMF) |
| 21A | 5 | 60.2 |
| 21B | 5 | 68.2 |
| 22A | 5 | 54.6 |
| 22B | 5 | 55.0 |
| 23A | 5 | 52.7 |
| 23B | 5 | 48.4 |
| 24A | 5 | 65.4 |
| 24B | 5 | 67.3 |
| 25A | 5 | 76.2 |
| 25B | 5 | 59.3 |
| | AVERAGE | 60.4 |
| | MIN | 48.4 |
| | MAX | 76.2 |

USE OF HERBS IN HAIR RELAXATION

FIELD OF THE INVENTION

This invention relates to a composition for relaxing human hair and to a method for relaxing human hair with minimal damage to the hair.

BACKGROUND OF THE INVENTION

Relaxers are chemical solutions used for the purpose of straightening, softening or loosening curled or wavy hair. Generally these chemical compositions contain soluble alkaline earth materials such as sodium or calcium hydroxide. Organic bases such as guanidine hydroxide are also employed as relaxers.

Sodium hydroxide, used in products referred to as "lye" relaxers, provides the longest lasting and dramatic effects. However, at a pH of about 14, solutions of sodium hydroxide have a pronounced tendency to damage the skin and hair.

Relaxers referred to as "no lye" systems have a lower pH of about 13. Nevertheless, such relaxers have the potential to weaken the hair making it extremely susceptible to breaking and further damage. For this reason, a pre-protective petroleum "base cream" is frequently applied to help protect the scalp against chemical irritation. After the hair has been chemically relaxed, a neutralizing formula may be applied to lower the pH and reduce the potential for hair breakage. Frequently, a conditioner is applied to the hair to restore some of the natural oils and proteins removed by the chemical.

"No lye" relaxers utilize the organic chemical base, guanidine, present in the form of guanidine hydroxide, as the straightening agent. The product is supplied as a two component system comprising first an aqueous solution of guanidine carbonate at or near the saturation point. The second component is a water in oil cream emulsion containing calcium hydroxide (inorganic alkaline earth hydroxide) at 3-8% typically by weight usually referred to as the "base". Upon mixing, the guanidine carbonate component of the activator solution reacts with the base, e.g., calcium hydroxide forming guanidine hydroxide and precipitated calcium carbonate.

Guanidine hydroxide is not stable after formation and decomposes into ammonia and urea within 6-12 hours after mixing. The guanidine hydroxide elevates the pH of the product to about 13 and thereby allows for successful relaxation of the hair. Products of this type normally do not require a pre-protective application of petrolatum or similar composition. These products are typically called "no-lye products".

The high pH relaxer compositions available today utilize very much the same chemistry in that they all rely on the generation of hydroxide to relax the hair. This high pH relaxation of the hair fiber is not without challenge to the formulator. Modern compositions contain skin protectants such as mineral oil and petrolatum, waxes, conditioning agents and humectants but the high pH of the relaxer cream base itself prevents the inclusion into the formula of ingredients that would have greater beneficial effect for the consumer. The typical relaxer base containing calcium hydroxide has a pH in the range of 11-12.5 before activation with guanidine carbonate. After activation, this pH will increase 15 fold but still, at a pH above 11 many organic and beneficial ingredients are destroyed. At this elevated pH only the most basic and chemically resistant materials survive for any length of time. While many modern products may include some organic materials in their relaxer creams or bases, the longevity and stability of these materials is very highly suspect at the pH mentioned above. As a result, many relaxers deliver poor performance and may irritate the skin if not used specifically as directed.

SUMMARY OF THE INVENTION

In view of the harmful effects of hair relaxation systems on the hair and skin, it is desirable to provide novel forms of treatment which safely and effectively relax, soften and straighten hair.

It is also desirable to overcome the above described problems and disadvantages of previously known hair relaxation systems by providing a cost effective, long-lasting, easy-to-apply system leaving the hair strong, healthy and natural looking.

In accordance with the purpose of the present invention as embodied and broadly described herein, the present invention relates to a method of applying a liquid preparation to the hair to achieve relaxation with no more than minimal damage.

The present invention provides a method of relaxing human hair comprising the steps of
  (a) preparing an aqueous mixture having a pH of at least 11 comprising
    (i) at least one base; and
    (ii) a pre-selected blend of dehydrated herbs;
  (b) applying the mixture to human hair for a period of time sufficient to effect a desired amount of relaxation; and
  (c) removing the mixture from the hair with a rinsing liquid.

In a particular embodiment an aqueous mixture is provided which is comprised of a base in the form of an aqueous emulsion of calcium hydroxide to which a combination of herbs is admixed.

In one embodiment of the present invention a hair relaxation preparation is provided which is comprised of an aqueous mixture of at least one base and a pre-selected blend of herbs wherein said base is a water-soluble alkali-metal hydroxide, an alkaline earth hydroxide or a water-soluble organic base and wherein said blend of herbs is comprised of *Apocynum Cannabinum* Root, *Urtica Dioica*, *Rosmarinus Officinalis* Leaf, *Arctium Lappa* Root, *Betula Alba*, *Rosa Canina* Fruit, *Chondrus Crispus*, *Tussilago Farfara* Flower, *Prunus Serotina* Bark, *Taraxacum Officinale*, *Sambucus Nigra*, *Equissetum Hiemale*, and *Echinacea Purpurea* and wherein said preparation has a pH of at least about 11.

In a particular embodiment the aqueous mixture further comprises an activator wherein said activator is the base guanidine hydroxide formed in situ by the reaction of guanidine carbonate with calcium hydroxide.

In one embodiment the present invention provides a method of relaxing human hair wherein said dehydrated blend of herbs is mixed with calcium hydroxide in an amount of 0.1 to 10.0 gm of herbs to about 200 gm of calcium hydroxide.

In another embodiment the calcium hydroxide, dehydrated herbs and aqueous solution of an activator (e.g., guanidine carbonate) are mixed in a ratio of about 200 gm calcium hydroxide base to about 0.25-0.4 gm dehydrated blend of herbs to about 59 ml of solution. In the particular embodiment where guanidine carbonate is used, the concentration of the guanidine carbonate in the solution is about 1.15 g/ml.

In another embodiment of the present invention a method of relaxing human hair is provided comprising the steps of
  (a) preparing an aqueous mixture having a pH of at least 11 comprising
    (i) at least one base; and
    (ii) a pre-selected blend of dehydrated herbs;

(b) applying the mixture to human hair for a period of time sufficient to effect a desired amount of relaxation; and
(c) removing the mixture from the hair with a rinsing liquid;
wherein said human hair retains from 60% to 99% of its original (i.e. untreated) tensile strength; in a preferred embodiment said human hair retains at least about 80% of its original tensile strength.

In another embodiment said aqueous mixture further comprises mineral oil and/or petrolatum and a surfactant.

In another embodiment said aqueous mixture further comprises a polyhydric alcohol.

In another embodiment of the present invention a method of relaxing human hair is provided comprising the steps of
(a) preparing an aqueous mixture having a basic pH comprising
(iii) at least one base; and
(iv) a pre-selected blend of dehydrated herbs;
(b) applying the mixture to human hair for a period of time sufficient to effect a desired amount of relaxation; and
(c) removing the mixture from the hair with a rinsing liquid.

BRIEF DESCRIPTION OF THE SEVERAL VIEWS OF THE DRAWINGS

FIG. 1 illustrates the break load of hair filaments treated only with shampoo and warm water rinses. The strand number refers to a single hair filament that was taken from a test swatch and subjected to a tensile strength test. The group number refers to a specific testing set of swatches that were subjected to a particular set of testing parameters. GMF, or grams of measured force, refers to the amount of force (in grams) required to pull a strand of hair to the breaking point and is indicative of the tensile strength value of that particular hair filament.

DETAILED DESCRIPTION OF THE INVENTION

The present invention provides a novel treatment system for effectively relaxing and straightening human hair with minimal damage and irritation to the scalp and hair.

Recognizing that relatively high pH solutions are needed to relax the curl or wave in human hair, the present inventors have found a new and surprisingly effective formulation which modulates and significantly reduces the damaging effects of high pH on the hair. Thus, for the first time, a safe and effective method is offered to those individuals who wish to cosmetically change the appearance, shape and ease of handling of their hair.

The present invention provides a novel method of relaxing human hair comprising the steps of
(a) preparing an aqueous mixture having a pH of at least 11 comprising
(v) at least one base; and
(vi) a pre-selected blend of dehydrated herbs;
(b) applying the mixture to human hair for a period of time sufficient to effect a desired amount of relaxation; and
(c) removing the mixture from the hair with a rinsing liquid.

The base, often referred to as the "relaxer base" is comprised of a water-soluble alkali-metal hydroxide, an alkaline earth hydroxide or a water-soluble organic base. Calcium hydroxide is the preferred base. Generally this relaxer base solution has pH of about 11. Prior to application to the hair, a blend of dehydrated herbs is mixed into the relaxer base solution. The blend of herbs is comprised of one or more of *Apocynum Cannabinum* Root, *Urtica Dioica*, *Rosmarinus Officinalis* Leaf, *Arctium Lappa* Root, *Betula Alba*, *Rosa Canina* Fruit, *Chondrus Crispus*, *Tussilago Farfara* Flower, *Prunus Serotina* Bark, *Taraxacum Officinale*, *Sambucus Nigra*, *Equissetum Hiemale*, and *Echinacea Purpurea* and wherein said preparation has a pH of at least about 11.

In order to raise the pH of the base-herb mixture to about 13-15 for effective hair relaxation, an additional base, generally referred to as an "activator", is optionally added to the mixture. A preferred "activator" is guanidine carbonate and more preferably guanidine carbonate in aqueous solution. The pH of the mixture is thus elevated through the reaction shown in Scheme I.

Scheme I
Guanidine carbonate+calcium hydroxide  Guanidine hydroxide+calcium carbonate The reaction occurs instantly at room temperature and elevates the pH of the mixture to a range of 13-15.

In its present use, the "activator" guanidine carbonate is provided as an aqueous solution that is premixed with the calcium hydroxide prior to application to the hair. The calcium hydroxide is usually referred to as the "relaxer base" and is typically provided at a pH of 11-12.5 dispersed in a water-in-oil emulsion containing additional skin protectants such as mineral oil, petrolatum, waxes and condition agent or humectants.

The basic pH of the relaxer hydrates and hydrolyzes the cellulose coating of the herbs and aids in the release of organic enzymes and chemicals that diffuse into the relaxer base at the time of use. The diffusion of these materials can be seen within several minutes of mixing as a slight striation within the white relaxer cream/activator/herb mixture at high pHs.

The relaxer base composition described above is an aqueous cosmetic emulsion of mineral oil and petrolatum in water that contains calcium hydroxide with emulsifiers and other surfactants. The primary emulsifier is most often a mixture of surfactants and fatty alcohols with a chain length of between 12 and 18 carbon atoms as part of the fatty component. Non-ionic, anionic emulsifiers and amphoteric emulsifiers or zwitterionic emulsifiers and conditioning agents that have been found to be stable at high pH such as polymeric quaternary nitrogen containing compounds may also be present. Polyhydric alcohols such as glycerine and propylene glycol may also be used with the total of these ingredients comprising approximately 50% of the composition of the base and the remaining 50% being water.

The relaxer composition described above utilizing the high pH extraction of the herbal ingredients provides superior conditioning, hair strengthening and overall performance when compared to relaxers without the herbal ingredients. Currently used, well-known relaxers of the type described herein lead to losses of hair strength of as much as 40-45%; whereas, the incorporation of dehydrated herbs as taught in the present invention leads to a retention of at least 80% of hair strength.

It should be noted that all references to % are made in weight percent throughout this disclosure.

The relaxer base may comprise any of a group of water-soluble alkali metal hydroxide or alkaline earth hydroxides. Single component relaxers are known in the market that do not require the addition of an activator and contain approximately 1.5-2.5% sodium hydroxide. The addition of the herbs to relaxers of this composition that do not require the addition of an activator (lye relaxers) also produce the desirable effects described.

An aspect of this invention is the preservation of the stability of these ingredients by maintaining the herbs in the dry, dehydrated form prior to dispersion in the relaxer solution before application to the hair. Upon mixing with the relaxer solution the herbs are reconstituted and hydrated permitting the subsequent extraction of the ingredients into the relaxer base. Preservation in the dehydrated state prior to use allows these ingredients to produce the full beneficial effects of performance, irritation reduction, hair strength retention and conditioning.

The existing processes by which hair is straightened weakens the hair, making it extremely susceptible to breakage and further damage. Thus, as the strongly basic chemicals penetrate the hair shaft and reach the inner cortical layer a loosening of the natural curl pattern occurs. However, this inner cortical layer is also irreversibly damaged upon exposure to the strong chemicals, and thus the strength and the elasticity of the hair is adversely affected.

Hair relaxers are not only potentially damaging to the hair, but also can be very irritating to the scalp. Frequently, as a precautionary measure, a protective petroleum "base cream" is applied to the scalp before relaxation to avoid or at least minimize exposure of the scalp to the relaxer chemicals.

After the relaxer chemical has been applied to the hair and left in contact for an appropriate period of time, the chemicals are removed by thorough rinsing with warm water. Optionally, a neutralizing agent is applied to bring the pH level of the hair back to normal levels.

To further aid in softening the hair and preventing future breakage, a conditioner comprising natural oil and proteins is optionally applied.

Suitable base compounds for use in the relaxer preparation include hydroxides of Group I or II metals. In addition to calcium hydroxide, basic compounds well-suited for use in the present invention include, but are not limited to, sodium hydroxide, potassium hydroxide, lithium hydroxide, magnesium hydroxide either alone or in combination.

Organic bases (e.g., amines), either alone or in combination with one or more of the above-mentioned Group I and II hydroxides, are also suitable for use in the relaxer preparation. Such bases include, but are not limited to, $C_2$-$C_{10}$ primary, secondary and tertiary amines.

The relaxer preparation is preferably water-based and the base compound is either water-soluble or readily water-dispersable with the aid of an emulsifier or surfactant. Among the emulsifiers and surfactant suitable for use in the present invention are the sodium, potassium or ammonium salts of $C_{12}$-$C_{18}$ carboxylic and sulfuric acids commonly referred to as anioic surfactants. Among the non-ionic surfactants useful in the present invention are the oxyethylated and oxypropylated derivatives of $C_{12}$-$C_{18}$ fatty alcohols. Cationic emulsifiers are also useful and these include, for example, polyamine and $C_{12}$-$C_{18}$ quaternary nitrogen compounds.

It is to be understood that the term "pre-selected blend of herbs" is used herein for purposes of the present invention to mean that any one or several or most or all of the herbs listed herein above. In a preferred aspect of the present invention all of the herbs listed hereinabove are added to the base preparation in the form of a dry mixture or optionally predispersed in water.

While not wishing to be bound by theory, the present inventors believe that under high pH conditions of the aqueous based relaxer, the cellulose outer shell structure of the herbs is softened and rendered more porous allowing internal enzymes and naturally occurring chemical component within the herb to diffuse out of the herb. In fact, the extraction and diffusion of these materials from within the herb structure can be observed with the unaided eye appearing as slight striations within the white colored relaxer mixture, which optionally contains an activator.

The term "pH" is herein used for the purpose of the present invention as a measure of acidity or alkalinity of a solution.

As is well-known to those skilled in the art, the formula for calculating pH is $$pH = -\log_{10} \alpha H^+$$

wherein $\alpha H^+$ denotes the activity of $H^+$ ions and is dimensionless. In dilute solution, such as those employed in the present invention, activity is approximately equal to the numeric value of the concentration of $H^+$ ions (more accurately expressed as $[H_3O^+]$) expressed in moles per liter.

Most solutions have a pH of about 1-14, with a pH of 14 considered extremely basic. Household lye, for example, has a pH of 13.5.

The invention is now described with reference to the following Examples. These Examples are provided for the purpose of illustration only, and the invention is not limited to these Examples, but rather encompasses all variations which are evident as a result of the teaching provided herein.

Example 1

Five swatches of curled and kinky hair samples (International Hair Importers & Products, Inc.) of equal weight and length were prepared. The swatches, identified as "NO RELAXATION" in FIG. 7, were rinsed with warm water and subjected to a shampoo using a total of two grams of African Pride® Neutralizing Conditioning Shampoo (Colomer USA, Jacksonville, Fla.). The swatch was subsequently rinsed. Each shampoo and rinse lasted one minute and was repeated once.

Figure 1:
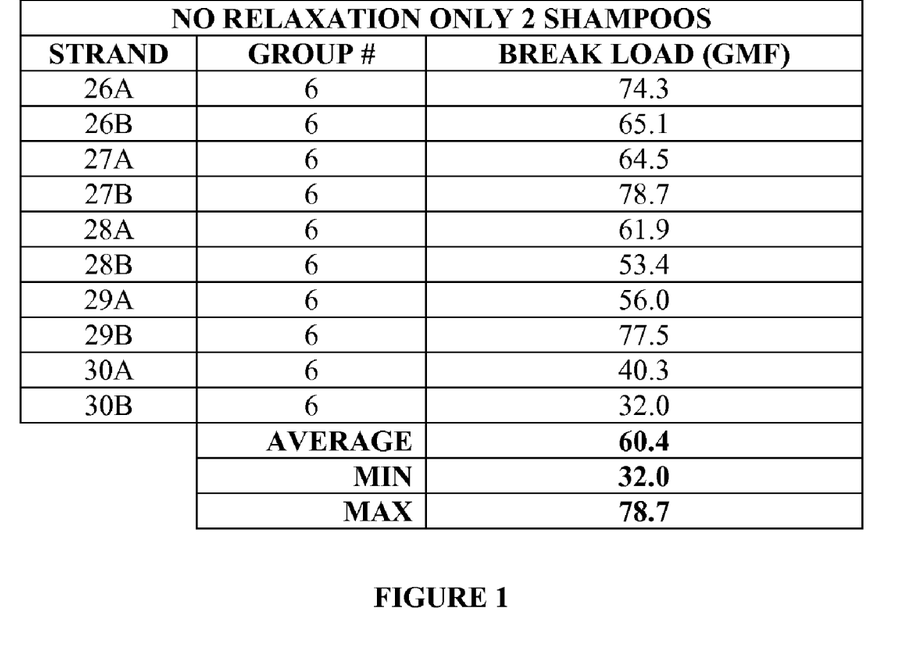

Two single hair filaments were removed from each swatch. Each hair strand was threaded and loaded into the Dia-stron MTT670 (Dia-Stron Ltd., Andover, UK) and subjected to a single fiber tensile test. Break loads, i.e. the force required to break a hair filament by pulling the ends in opposite directions, were obtained for each sample using MttWin version 6.0 Software (Dia-Stron Ltd., Andover, UK). The results of the single fiber tensile test are shown in FIG. 1. The average break load, measured in grams of force (GMF), was 60.4 with a minimum value of 32.0 and a maximum value of 78.7. The break loads of a few particular strands, indicated as " - - - ", were not obtainable (e.g., due to the hair strand breaking or prematurely releasing due to slippage from the Dia-stron restraining clip).

Example 2

Five swatches of curled and kinky hair samples of equal weight and length were prepared as described in Example 1.

Figure 7:
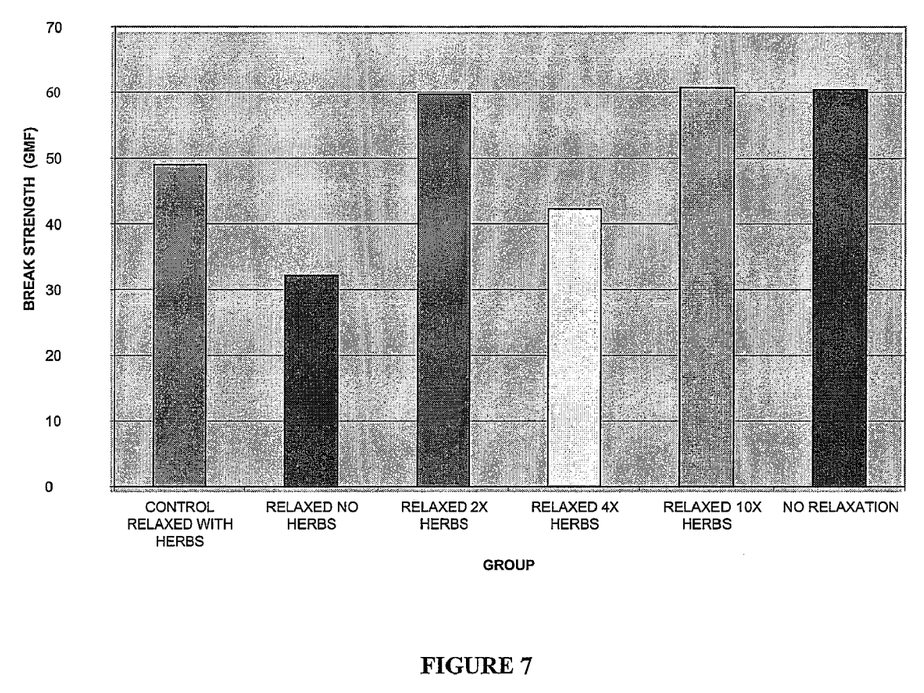
FIG. 7 is a comparison of the average break load of the six groups of hair filaments illustrated in FIGS. 1 through 6.

However, the swatches, identified as "RELAXED NO HERBS" in FIG. 7, were treated for twenty minutes with 10 grams of African Pride® No-Lye Conditioning Crème and Liquid Activator (Colomer USA, Jacksonville, Fla.) prior to the warm water rinse and shampoo steps. The African Pride® No-Lye Conditioning Crème and Liquid Activator was provided in the form a relaxer kit containing 201 grams of Conditioning Crème and 62 grams of Activator, which are mixed together prior to application.

Figure 2:
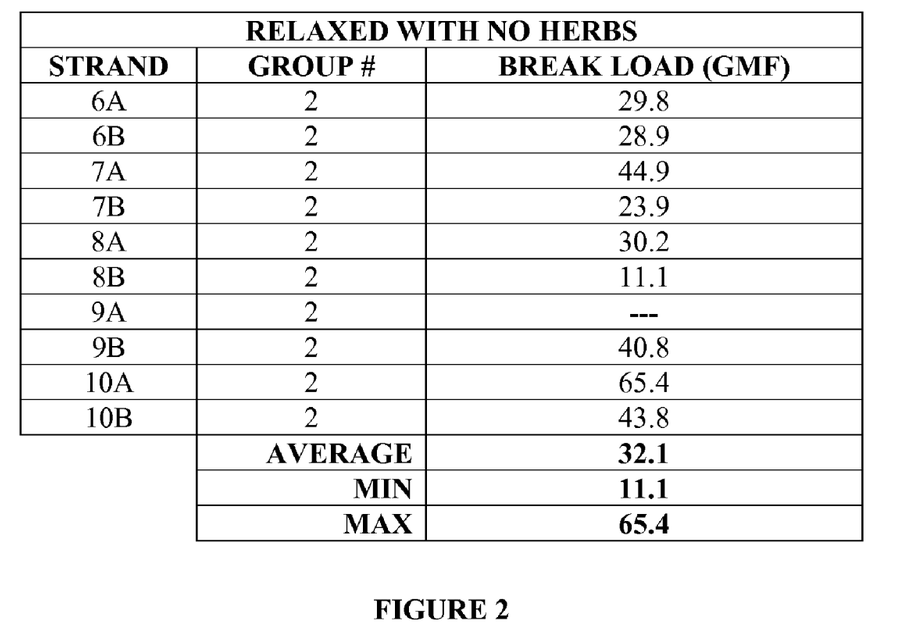
FIG. 2 illustrates the break load of hair filaments treated with activator prior to shampoo and warm water rinses.

The results of the single fiber tensile test are shown in FIG. 2. The resulting "relaxed" hair had an average break load of 32.1 with a minimum value of 11.1 and a maximum value of 65.4. Thus, the "relaxed" hair retained only about 53%, on the average, of its original strength.

Example 3

Five swatches of curled and kinky hair samples (International Hair Importers & Products, Inc.) of equal weight and length were prepared as described in Example 2. However, the swatches, identified as "CONTROL RELAXED WITH HERBS" in FIG. 7, were simultaneously treated with 0.35 grams of a dry herbal mixture and African Pride® No-Lye Conditioning Crème and Liquid Activator prior to the warm water rinse and shampoo steps. The herbal mixture consisted of *Apocynum Cannabinum* Root, *Urtica Dioica*, *Rosmarinus Officinalis* Leaf, *Arctium Lappa* Root, *Betula Alba*, *Rosa Canina* Fruit, *Chondrus Crispus*, *Tussilago Farfara* Flower, *Prunus Serotina* Bark, *Taraxacum Officinale*, *Sambucus Nigra*, *Equissetum Hiemale*, and *Echinacea Purpurea*.

Figure 3:
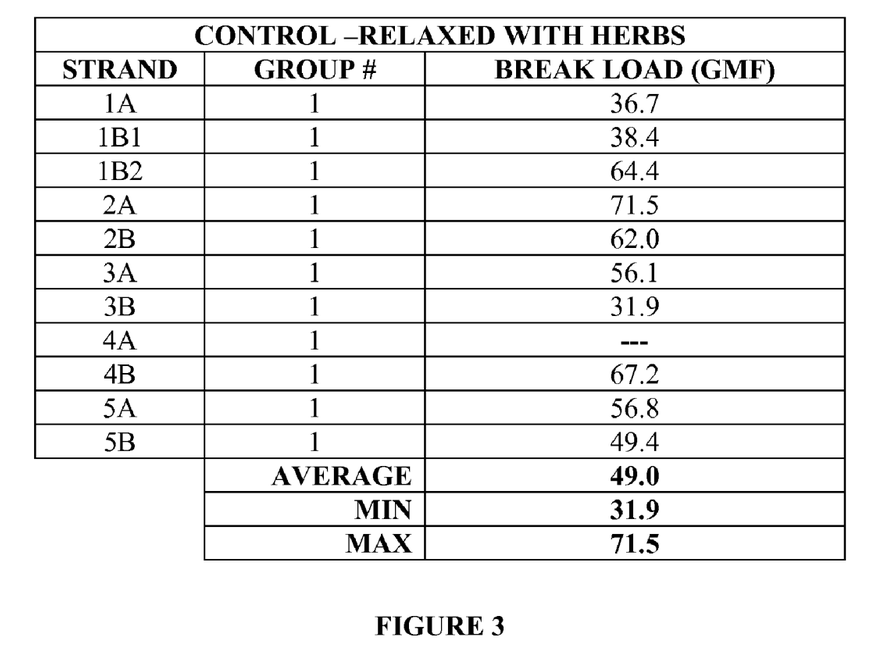
FIG. 3 illustrates the break load of hair filaments simultaneously treated with activator and 0.35 grams of an herbal mixture prior to shampoo and warm water rinses.

The results of the single fiber tensile test are shown in FIG. 3. The average break load was 49.0 with a minimum of 31.9 and a maximum of 71.5. Thus, hair relaxed in the presence of the herbal mixture retained about 81% of its original strength and was 1.5 times stronger than hair relaxed without the herbal mixture.

Example 4

Five swatches of curled and kinky hair samples of equal weight and length were prepared as described in Example 3. However, the swatches, identified as "RELAXED 2× HERBS" in FIG. 7, were simultaneously treated with 0.70 grams of the dry herbal mixture described in Example 3 and African Pride® No-Lye Conditioning Crème and Liquid Activator prior to the warm water rinse and shampoo steps.

Figure 4:
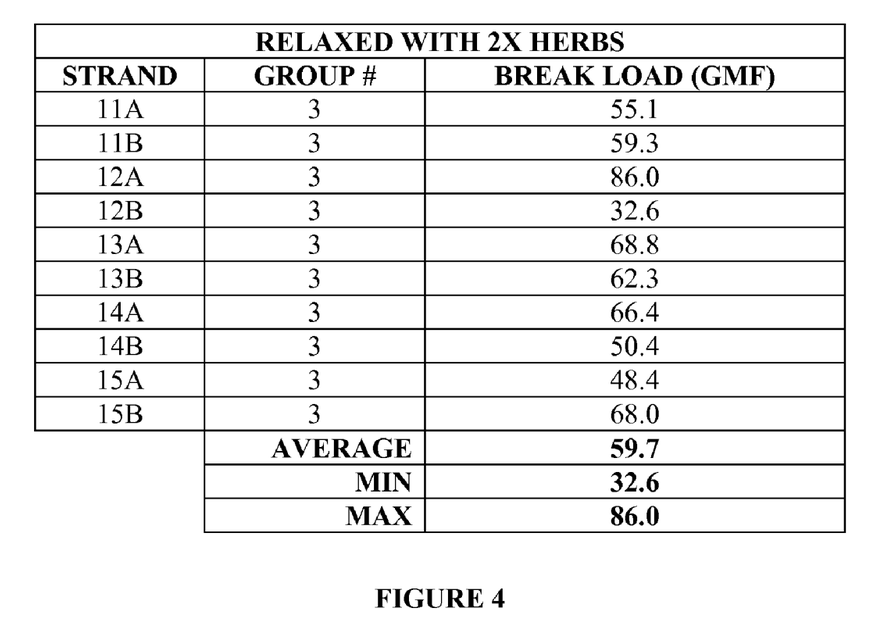
FIG. 4 illustrates the break load of hair filaments simultaneously treated with activator and 0.70 grams of an herbal mixture prior to shampoo and warm water rinses.

The results of the single fiber tensile test are shown in FIG. 4. The average break strength was about 59.7 with a minimum of 32.6 and a maximum of 86.0. Hair relaxed with twice the level of herbal mixture as that of Example 3 retained about 99% of its original strength and was 1.9 times stronger than hair relaxed without the herbal mixture.

Example 5

Five swatches of curled and kinky hair samples of equal weight and length were prepared as described in Example 3. However, the swatches, identified as "RELAXED 4× HERBS" in FIG. 7, were simultaneously treated with 1.4 grams of the dry herbal mixture described in Example 3 and African Pride® No-Lye Conditioning Crème and Liquid Activator prior to the warm water rinse and shampoo steps.

Figure 5:
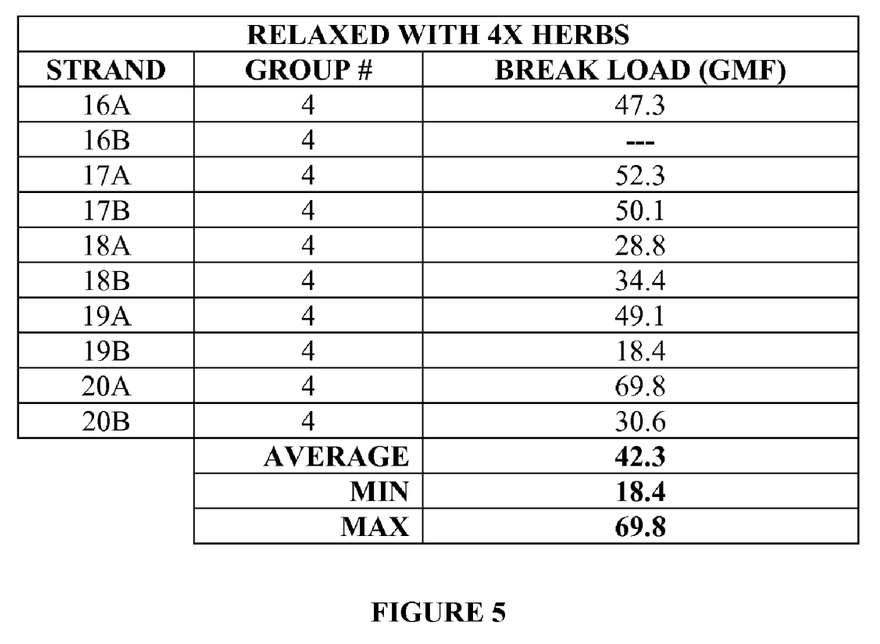
FIG. 5 illustrates the break load of hair filaments simultaneously treated with activator and 1.40 grams of an herbal mixture prior to shampoo and warm water rinses.

The results of the single fiber tensile test are shown in FIG. 5. The average break load was 42.3 with a minimum of 18.4 and a maximum of 69.8. Hair relaxed with four times the level of herbal mixture as that of Example 3 retained about 86% of its original strength and was 1.3 times stronger than hair relaxed without the herbal mixture.

Example 6

Five swatches of curled and kinky hair samples of equal weight and length were prepared as described in Example 3. However, the swatches, identified as "RELAXED 10× HERBS" in FIG. 7, were simultaneously treated with 3.5 grams of the dry herbal mixture described in Example 3 and African Pride® No-Lye Conditioning Crème and Liquid Activator prior to the warm water rinse and shampoo steps.

Figure 6:
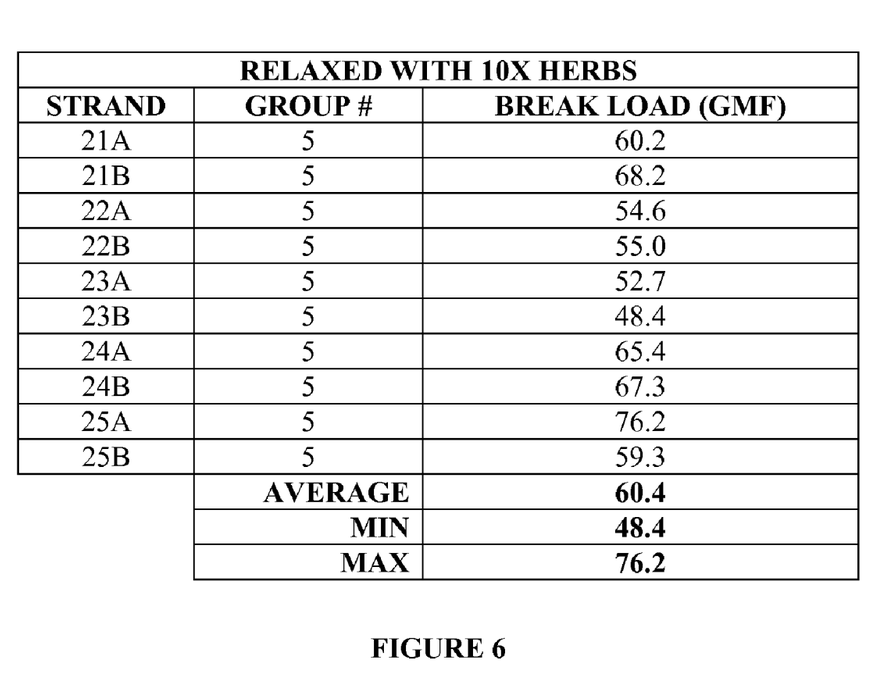
FIG. 6 illustrates the break load of hair filaments simultaneously treated with activator and 3.50 grams of an herbal mixture prior to shampoo and warm water rinses.

The results of the single fiber tensile test are shown in FIG. 6. The average break load was 60.4 with a minimum of 48.4 and a maximum of 76.2. Hair relaxed with ten times the level of herbal mixture as that of Example 3 retained about 100% of its original strength and was 1.9 times stronger than hair relaxed without the herbal mixture.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of relaxing human hair comprising
preparing an aqueous mixture having a pH of at least 11 comprising
at least one base; and
a pre-selected blend of dehydrated herbs comprising *Apocynum Cannabinum* Root, *Urtica Dioica*, *Rosmarinus Officinalis* Leaf, *Arctium Lappa* Root, *Betula Alba*, *Rosa Canina* Fruit, *Chondrus Crispus*, *Tussilago Farfara* Flower, *Prunus Serotina* Bark, *Taraxacum Officinale*, *Sambucus Nigra*, *Equissetum Hiemale*, and *Echinacea Purpurea*;
applying the mixture to human hair for a period of time sufficient to effect a desired amount of relaxation; and
removing the mixture from the hair with a rinsing liquid.

2. The method according to claim 1 wherein said aqueous mixture contains a base in the form of a water-soluble alkali metal hydroxide, an alkaline earth hydroxide or an water soluble organic base or combinations thereof.

3. The method according to claim 2 wherein said base is calcium hydroxide.

4. The method of relaxing human hair according to claim 1 wherein said aqueous mixture contains the base calcium hydroxide and further comprises an activator solution which comprises the base guanidine hydroxide formed in situ by the reaction of guanidine carbonate with calcium hydroxide in water.

5. The method according to claim 1 wherein said aqueous mixture further comprises mineral oil and/or petrolatum and a surfactant.

6. The method according to claim 1 wherein said aqueous mixture further comprises a polyhydric alcohol.

7. A cosmetic formulation for relaxing human hair comprising:
an aqueous mixture of a base and a pre-selected blend of dehydrated herbs comprising *Apocynum Cannabinum* Root, *Urtica Dioica*, *Rosmarinus Officinalis* Leaf, *Arctium Lappa* Root, *Betula Alba*, *Rosa Canina* Fruit, *Chondrus Crispus*, *Tussilago Farfara* Flower, *Prunus*

*Serotina* Bark, *Taraxacum Officinale, Sambucus Nigra, Equissetum Hiemale*, and *Echinacea Purpurea,*
wherein said base is a water-soluble alkali metal hydroxide, an alkaline earth hydroxide or a water soluble organic base and combinations thereof, wherein said aqueous mixture has a pH of at least 11.

8. The cosmetic formulation for relaxing the hair according to claim 7 further comprising the base guanidine hydroxide, an activator, formed in situ by the reaction of guanidine carbonate with calcium hydroxide.

9. The method of relaxing human hair according to claim 1 wherein said dry blend of herbs is mixed with said base in an amount of 0.1 to 10.0 gm of dry herb to about 200 gm of said base.

10. The method of relaxing human hair according to claim 1 wherein said human hair retains from 60% to 99% its original tensile strength.

11. The method of relaxing human hair according to claim 1 wherein said human hair retains at least about 80% of its original untreated tensile strength.

12. The method of relaxing human hair according to claim 4 wherein said base, dry herbs and activator are mixed in an amount of 200 gm relaxer base to 0.25-0.4 gm dry herbs to about 54 ml of activator solution said activator solution having a concentration of about 54 gm activator per 62 ml of solution.

13. The method according to claim 1 wherein the aqueous mixture has a pH of 12-14.

14. The method according to claim 2 wherein said base and said blend of herbs are pre-mixed and subsequently added to the activator.

15. A method of relaxing human hair comprising:
preparing an aqueous mixture having a basic pH comprising
at least one base; and
a pre-selected blend of dehydrated herbs comprising *Apocynum Cannabinum* Root, *Urtica Dioica, Rosmarinus Officinalis* Leaf, *Arctium Lappa* Root, *Betula Alba, Rosa Canina* Fruit, *Chondrus Crispus, Tussilago Farfara* Flower, *Prunus Serotina* Bark, *Taraxacum Officinale, Sambucus Nigra, Equissetuin Hiemale*, and *Echinacea Purpurea;*
applying the mixture to human hair for a period of time sufficient to effect a desired amount of relaxation; and
removing the mixture from the hair with a rinsing liquid.

* * * * *

UNITED STATES PATENT AND TRADEMARK OFFICE
CERTIFICATE OF CORRECTION

| | | |
|---|---|---|
| PATENT NO. | : 8,025,909 B2 | Page 1 of 1 |
| APPLICATION NO. | : 12/176285 | |
| DATED | : September 27, 2011 | |
| INVENTOR(S) | : David Jarvis et al. | |

It is certified that error appears in the above-identified patent and that said Letters Patent is hereby corrected as shown below:

On title page, item (75) Inventor
insert --Ashraf Hossain, Arlington Heights, IL (US)-- as a co-inventor.

Signed and Sealed this
Twenty-ninth Day of November, 2011

David J. Kappos
*Director of the United States Patent and Trademark Office*